(12) United States Patent
Soroushian et al.

(10) Patent No.: US 6,509,056 B2
(45) Date of Patent: Jan. 21, 2003

(54) PREPARATION OF CONCRETE SAMPLES FOR MICROSCOPIC ANALYSIS

(75) Inventors: Parviz Soroushian, Lansing, MI (US); Ali Nossoni, Lansing, MI (US)

(73) Assignee: DPD, Inc., Lansing, MI (US)

(*) Notice: Subject to any disclaimer, the term of this patent is extended or adjusted under 35 U.S.C. 154(b) by 57 days.

(21) Appl. No.: 09/877,449

(22) Filed: Jun. 11, 2001

(65) Prior Publication Data

US 2002/0187274 A1 Dec. 12, 2002

(51) Int. Cl.[7] ................................................. B05D 5/12
(52) U.S. Cl. ........................... 427/8; 427/230; 427/294; 427/384; 702/35
(58) Field of Search ................................ 427/333, 157, 427/230, 238, 256, 258, 294, 372.2, 384, 402, 407.1, 8; 364/552; 702/35

(56) References Cited

U.S. PATENT DOCUMENTS 5,262,967 A * 11/1993 Jaber et al. ................. 356/626

* cited by examiner

*Primary Examiner*—Michael Barr
*Assistant Examiner*—Rebecca A. Blanton

(57) ABSTRACT

Concrete materials are impregnated with liquids which harden within concrete pores and microcracks, and develop a sharp contrast with the body of concrete in microscopic images. The impregnation process involves vacuum application to remove air from concrete pores and microcracks, followed by the introduction of liquids under pressure. The sharp contrast between the impregnated (and hardened) liquid and the body of concrete facilitates distinction of pores and microcracks in microscopic images for the purpose of automated image analysis.

19 Claims, 4 Drawing Sheets

PREPARATION OF CONCRETE SAMPLES FOR MICROSCOPIC ANALYSIS

This invention was made with U.S. government support under Contract F08630-00-C-0025 by U.S. Air Force. The U.S. government has certain rights in the invention.

BACKGROUND OF THE INVENTION

1. Field of the Invention

The invention is generally related to microscopic analysis of concrete. Particularly, the invention is directed to a great improvement of the contrast of concrete cracks and air voids versus the body of concrete for the purpose of automated analysis of concrete microscopic images.

2. Description of the Relevant Art

Air voids and cracks strongly influence the durability and mechanical attributes of concrete. Microscopic techniques are used to analyze the pore system and cracking characteristics of concrete. Available techniques rely on an operator who visually identifies concrete pores and cracks under microscope. U.S. Pat. No. 5,262,967 to Jaber and Pearson discloses a system and method for determining the air-void or aggregate content of concrete under microscope. This system requires an operator to identify features of interest (voids and aggregates) under microscope. In order to apply modern image analysis techniques to microscopic investigation of concrete, there is a need to create a sharp contrast between features of interest (air voids and cracks) and the body of concrete in microscopic images.

SUMMARY OF THE INVENTION

It is an object of this invention to provide concrete microscopic images which exhibit a sharp contrast between air voids and cracks versus the body of concrete.

It is another object of this invention to impregnate concrete with liquids which harden within concrete pores and cracks, and produce a sharp contrast with the body of concrete under microscope.

It is another object of this invention to impregnate concrete with liquids which preferentially fill air voids and cracks, but not capillary pores, with substances exhibiting a sharp contrast with the body of concrete.

Applicant has discovered that, for the purpose of fluorescent microscopy, sequential impregnation of concrete first with an ink and then with a polymer containing fluorescent dye mitigates impregnation of capillary pores with fluorescent-containing polymer. Only air voids and cracks are thus impregnated with polymer containing fluorescent dye. After curing of the polymer, therefore, fluorescent cracks and pores exhibit a sharp contrast against the body of concrete in fluorescent micrographs.

For the purpose of scanning electron microscopy, impregnation of concrete with molten metal fills cracks and air voids, but not the capillary pores, with molten metal. After solidification of molten metal scanning electron microscopic images of concrete exhibits sharp contrast between air voids and cracks (which are filled with metal) against the body of concrete.

According to the invention, there is provided concrete impregnation techniques which produce a sharp contrast between air voids and cracks against the body of concrete.

DETAILED DESCRIPTION OF THE PREFERRED EMBODIMENTS OF THE INVENTION

Air voids ranging in size from 50 to 1000 micron as well as cracks are major features of concrete microstructure. Application of modern image analysis techniques for identification and quantification of concrete air voids and cracks requires staining of these features so that they can be easily identified under microscope; staining should produce a sharp contrast between features of interest (air voids and cracks) and the body of concrete.

Staining of concrete can be accomplished through impregnation with liquids that harden within cracks and voids; the hardened material then exhibits a sharp contrast with the body of concrete in microscopic images. Polymers (e.g., epoxies) incorporating fluorescent dye, for example, can be used to impregnate concrete.

The cement paste in concrete comprises an interconnected network of capillary pores which range in size from 0.01 to 5 micron. Impregnation of concrete, therefore, not only fills the features of interest (air voids and cracks) but also the capillary pores in concrete. This diminishes the contrast needed to distinguish the features of interest from the body of concrete. For example, when concrete is impregnated with fluorescent epoxy, fluorescent microscopy yields images similar to that shown in FIG. 1. The fact that not only cracks and air voids but also the capillary pores of cement paste are impregnated with fluorescent epoxy reduces the contrast between features of interest (cracks and voids) and the body of concrete. This complicates distinction of cracks and voids from the body of concrete in automated image analysis procedures.

The problem described above can be overcome using a two-step impregnation. Concrete is first impregnated with a material that can solidify only in fine capillary pores (0.01 to 5 micron in size) but not in coarser air voids or cracks; ink is a simple and readily available example of such liquids. In subsequent impregnation of concrete with fluorescent epoxy, therefore, only cracks and air voids will be available to be stained with fluorescent epoxy. This two-step impregnation of concrete, first with ink and (after curing of ink) with fluorescent epoxy, yields fluorescent microscope images similar to that shown in FIG. 2. Cracks and air voids show a sharp contrast with the body of concrete in this image, and can thus be conveniently and precisely recognized in automated image analysis routines.

In order to avoid staining of capillary pores during impregnation, one can also use a non-wetting liquid which cannot impregnate and solidify within finer (0.01–5 micron) capillary pores. Wood's metal (an alloy of bismuth, lead, tin and cadmium) is an example of such non-wetting liquids (with effective surface tension of about 400 mN/m.

Figure 2:
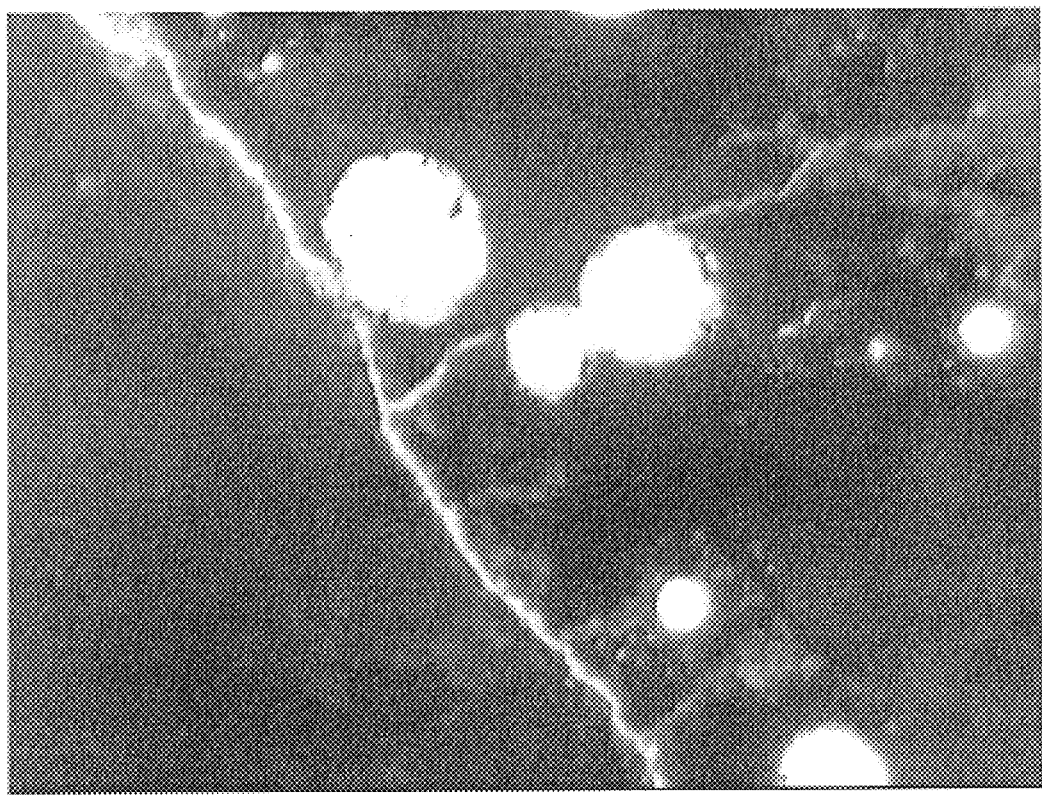
FIG. 2 is a typical image of concrete impregnated first with ink and then with fluorescent epoxy, observed under fluorescent microscope (at 210×magnification).

Impregnation of concrete with molten Wood's metal thus stains only the features of interest (air voids and cracks) and produces a sharp contrast between such impregnated features and the body of concrete in images captured under scanning electron microscope, as shown in FIG. 2.

Figure 3:
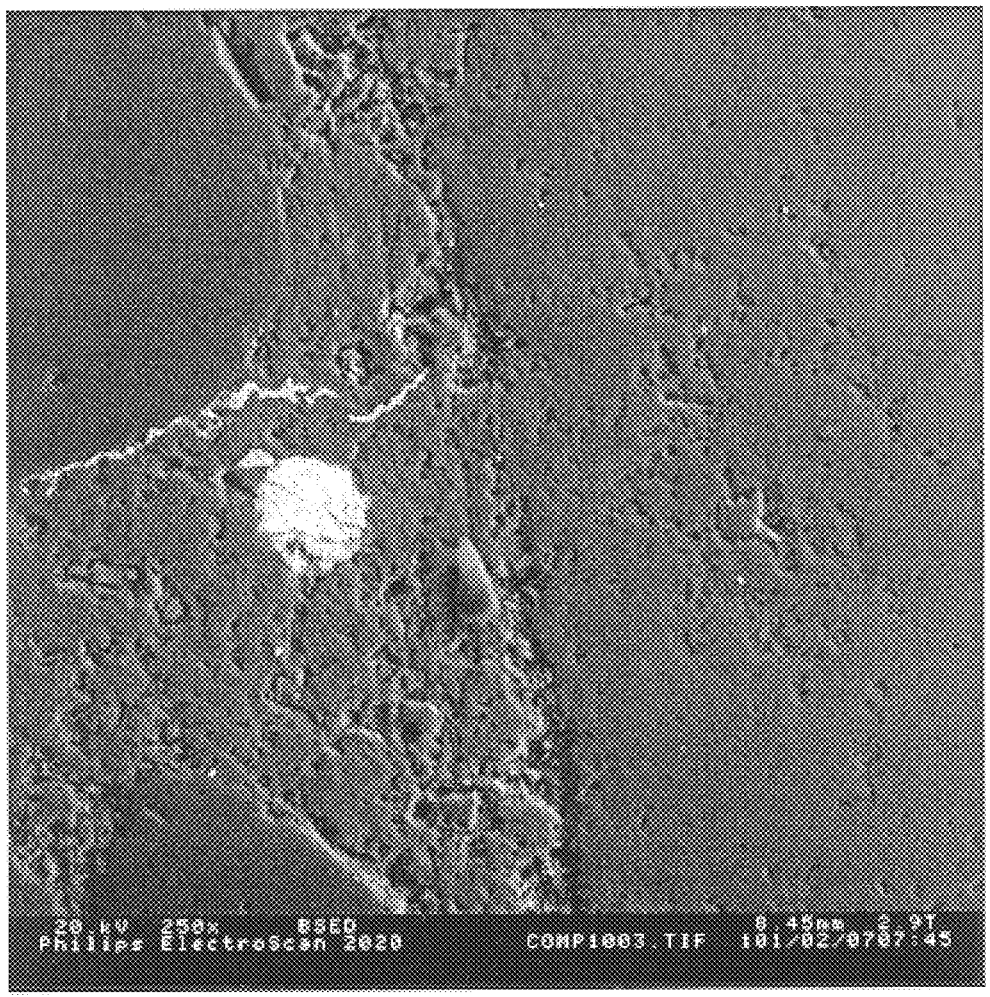
FIG. 3 is a typical image of concrete impregnated with molten Wood's metal, observed under scanning electron microscope (at 250×magnification).

Another approach involves impregnation of concrete first with Wood's metal (to fill air voids and cracks) and then with fluorescent epoxy (to stain the body of concrete). This also creates a contrast between the body of concrete (impregnated with fluorescent epoxy) and cracks and air voids (impregnated with Wood's metal) under fluorescent microscope, as shown in FIG. 3.

INVENTION AND COMPARISON EXAMPLES

Example 1

Figure 1:
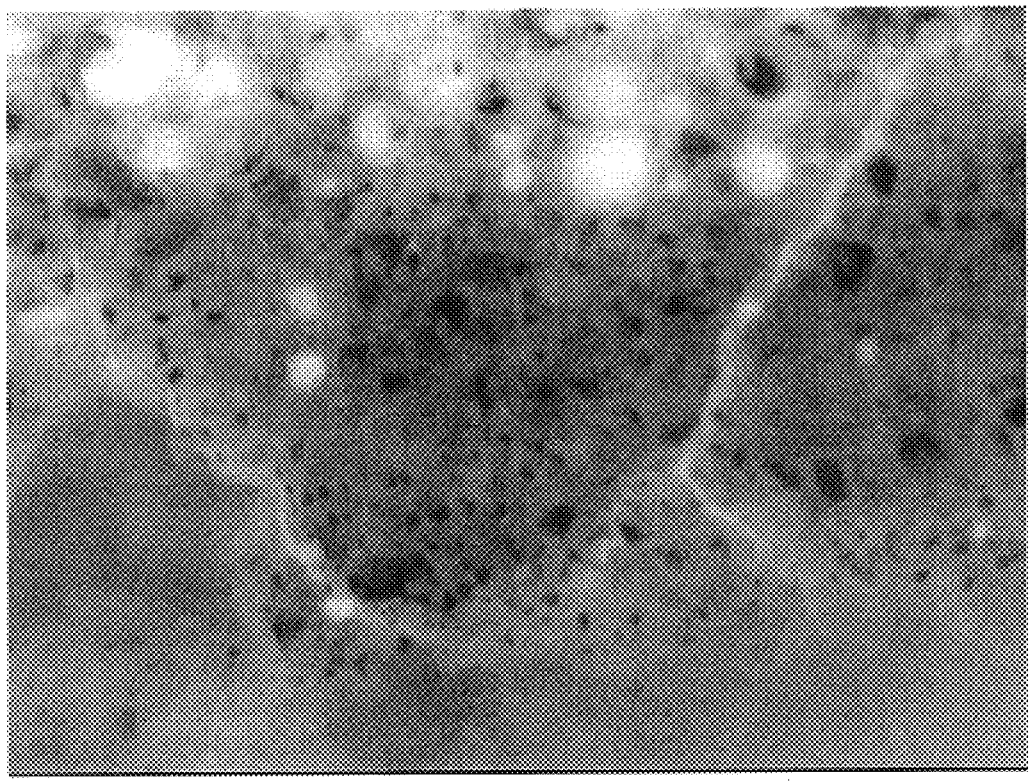
FIG. 1 is a typical image of concrete impregnated with fluorescent epoxy, observed under fluorescent microscope (at 210×magnification).

A normal-strength concrete sample was cut to a cylindrical slice with diameter of 100 mm and thickness of 25 mm. This sample was lapped, washed with tap water and soap, and dried at 60° C. for 4 hours. The sample was then placed in a glass flask connected to a vacuum, subjected to 2.7 KPa vacuum for one hour, and immersed in fluorescent epoxy. The fluorescent epoxy comprised a low-viscosity epoxy, hardener, and 3% by weight of fluorescent dye (solvent yellow 43). After immersion of the concrete sample in fluorescent epoxy, vacuum was turned off and the immersed concrete sample was transferred to a pressure chamber where it was subjected to 1 MPa pressure for 4 hours. The sample was subsequently placed at 60° C. for 24 hours in order to cure the epoxy, and its surface was lapped. The fluorescent microscopic image of this sample is shown in FIG. 1. Air voids and cracks can be observed in this image; however, due to the impregnation of capillary pores, there is no sharp contrast between the body of concrete and the features of interest (air voids and cracks). This sharp contrast is critical if automated image analysis procedures are to be applied to the image.

Example 2

A normal-strength concrete sample was cut to a cylindrical slice with diameter of 100 mm and thickness of 25 mm. This sample was lapped, washed with tap water and soap, and dried at 60° C. for 4 hours. The sample, placed in a container, was placed in a glass flask connected to vacuum, and vacuum-dried for one hour under a vacuum of 2.7 MPa. The container was then filled with a diluted ink comprising 60% by weight of Parker Quink and 40% by weight of water. The vacuum was turned off, and the immersed sample was transferred to a pressure chamber where it was subjected to nitrogen gas at pressure of 1.94 MPa for 18 hours. The sample was then placed in oven at 60° C. for 24 hours to ensure curing of the ink. The sample was then placed in a glass flask connected to a vacuum, subjected to 2.7 KPa vacuum for one hour, and immersed in fluorescent epoxy. The fluorescent epoxy comprised a low-viscosity epoxy, hardener, and 3% by weight of fluorescent dye (solvent yellow 43). After immersion of the concrete sample in fluorescent epoxy, vacuum was turned off and the immersed concrete sample was transferred to a pressure chamber where it was subjected to 1 MPa pressure for 4 hours. The sample was subsequently placed at 60° C. for 24 hours in order to cure the epoxy, and its surface was lapped. The fluorescent microscopic image of this sample is shown in FIG. 2. The initial impregnation with ink is observed to prevent subsequent penetration of fluorescent epoxy into the body of concrete. Only air voids and cracks (which are the features of interest) are highlighted, and there is a sharp contrast between the body of concrete and the features of interest (air voids and cracks). A comparison of FIG. 1 with FIG. 2 clearly reveals the advantages of first impregnating concrete with ink and then with fluorescent epoxy. The sharp contrast shown in FIG. 2 between the features of interest (air voids and cracks) and the body of concrete is a major advantage in application of automated image analysis procedures to quantitative analysis of concrete air voids and cracks.

Example 3

A normal-strength concrete sample was cut to a cylindrical sample with 100 mm diameter and 35 mm thickness. The sample was washed with soap and tap water, and dried in oven at 60° C. for 24 hours. The sample was then placed in a steel container, covered with Wood's metal chips, and placed in a chamber where is was subjected to 6.65 KPa vacuum at 90° C. for 2 hours. The vacuum was then turned off, and nitrogen gas was introduced into the heated chamber at 1.94 MPa pressure for a period of 2 hours. Pressure and heat were then turned off, and the sample was allowed to cool down to room temperature. A thickness of 5 mm was then sawn off from the concrete surface, and the surface was lapped with abrasive paper and observed under scanning electron microscope. A typical microscopic image of this sample is shown in FIG. 3, where features of interest (cracks and voids) exhibit a sharp contrast with the body of concrete.

Exampe 4

Figure 4:
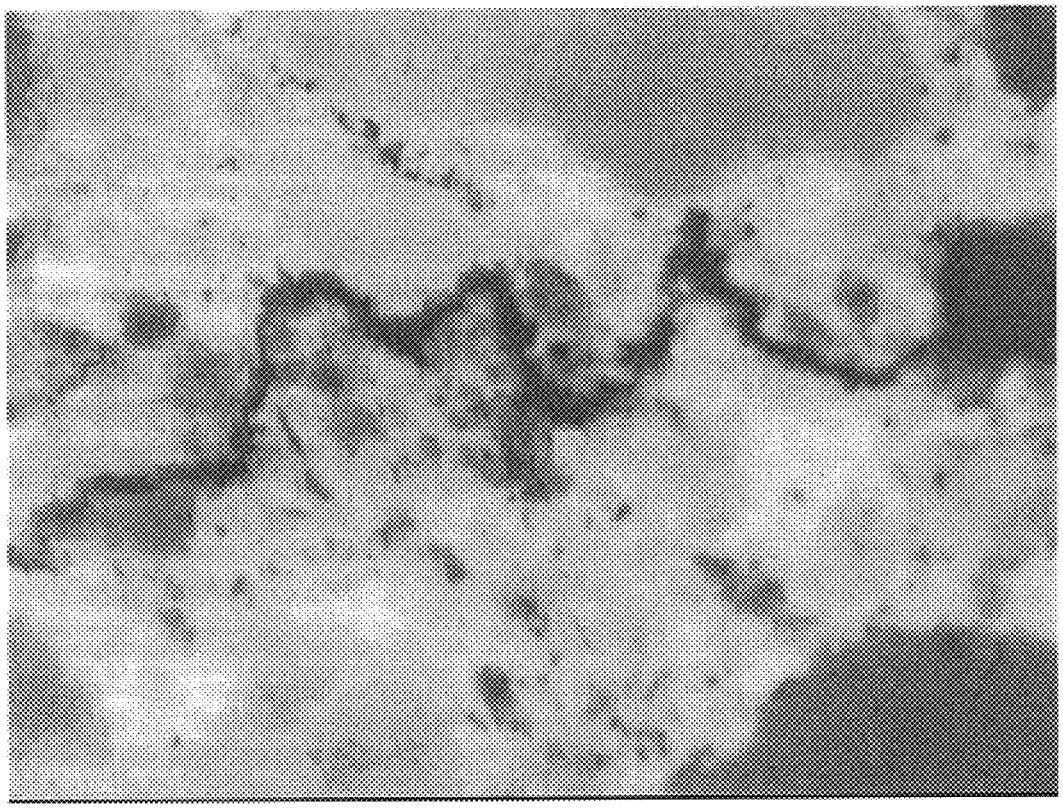
FIG. 4 is a typical image of concrete impregnated first with molten Wood's metal and then with fluorescent epoxy, observed under fluorescent microscope (at 210× magnification).

A normal-strength concrete sample was cut to a cylindrical sample with 100 mm diameter and 35 mm thickness. The sample was washed with soap and tap water, and dried in oven at 60° C. for 24 hours. The sample was then placed in a steel container, covered with Wood's metal chips, and placed in a chamber where is was subjected to 6.65 KPa vacuum at 90° C. for 2 hours. The vacuum was then turned off, and nitrogen gas was introduced into the heated chamber at 1.94 MPa pressure for a period of 2 hours. Pressure and heat were then turned off, and the sample was allowed to cool down to room temperature. This sample was then lapped, washed with tap water and soap, and dried at 60° C. for 4 hours. The sample was placed in a glass flask connected to a vacuum, subjected to 2.7 KPa vacuum for one hour, and immersed in fluorescent epoxy. The fluorescent epoxy comprised a low-viscosity epoxy, hardener, and 3% by weight of fluorescent dye (solvent yellow 43). After immersion of the concrete sample in fluorescent epoxy, vacuum was turned off and the immersed concrete sample was transferred to a pressure chamber where it was subjected to 1 MPa pressure for 4 hours. The sample was subsequently placed at 60° C. for 24 hours in order to cure the epoxy, and its surface was lapped. The fluorescent microscopic image of this sample is shown in FIG. 4. A comparison of FIG. 1 with FIG. 4 shows the advantages of first impregnating concrete with Wood's metal and then with fluorescent epoxy. There is a sharp contrast in FIG. 4 between the features of interest (air voids and cracks) and the body of concrete, which is a major advantage in application of automated image analysis procedures to quantitative analysis of concrete air voids and cracks.

We claim:
1. A method of impregnation concrete for the purpose of creating a sharp contrast within cracks and air voids against the body of concrete in microscopic images, comprising the steps of: (1) impregnating concrete with a liquid material which hardens within capillary pores but cannot solidify in bulk form within cracks and voids; and (2) impregnating concrete with another liquid material which solidifies within cracks and air voids and creates the contrast against the body of concrete in microscopic images.

2. A concrete impregnation method according to claim 1, wherein said liquid material which hardens within capillary pores is latex polymer.

3. A concrete impregnation method according to claim 1, wherein said liquid material which hardens within capillary pores is ink.

4. A concrete impregnation method according to claim 1, wherein said liquid material which solidifies within cracks and air voids is fluorescent polymer.

5. A concrete impregnation method according to claim 1, wherein said liquid material which solidifies within cracks and air voids is fluorescent epoxy comprising epoxy resin, hardener, and fluorescent dye.

6. A concrete impregnation method according to claim 1, wherein said impregnation processes involve application of at least one of heat, vacuum and pressure.

7. A concrete impregnation method according to claim 1, wherein said microscopic images are produced using fluorescent microscope on surfaces of prepared concrete samples subjected to at least one of cutting and polishing processes.

8. A method of impregnation concrete for the purpose of creating a sharp contrast within cracks and air voids against the body of concrete in microscopic images, comprising the steps of: (1) impregnating concrete with a liquid material which solidifies within cracks and air voids but cannot impregnate capillary pores; and (2) impregnating concrete with another liquid material which hardens within capillary pores and develops a sharp contrast against cracks and air voids.

9. A concrete impregnation method according to claim 8, wherein said liquid material which solidifies within cracks and air voids is molten metal.

10. A concrete impregnation method according to claim 8, wherein said liquid material which solidifies within cracks and voids is molten Wood's metal.

11. A concrete impregnation method according to claim 8, wherein said liquid material which hardens within capillary pores is fluorescent polymer.

12. A concrete impregnation method according to claim 8, wherein said liquid material which hardens within capillary pores is fluorescent epoxy comprising epoxy resin, hardener and fluorescent dye.

13. A concrete impregnation method according to claim 8, wherein said impregnation processes involve application of at least one of heat, vacuum and pressure.

14. A concrete impregnation method according to claim 8, wherein said microscopic images are produced using fluorescent microscope on surfaces of prepared concrete samples subjected to at least one of cutting and polishing processes.

15. A method of impregnating concrete for the purpose of crating a sharp contrast within cracks and air voids against the body of concrete in microscopic images, where concrete is impregnated with a liquid material which solidifies within cracks and air voids but cannot impregnate capillary pores.

16. A concrete impregnation method according to claim 15, wherein said liquid material is molten metal.

17. A concrete impregnation method according to claim 15, wherein said liquid material is molten Wood's metal.

18. A concrete impregnation method according to claim 15, wherein said impregnation process involves application of at least one of heat, vacuum and pressure.

19. A concrete impregnation method according to claim 15, wherein said microscopic images are produced using scanning electron microscope on surfaces of prepared concrete samples subjected to at least one of cutting and polishing processes.

\* \* \* \* \*